United States Patent
Ralph et al.

(10) Patent No.: US 8,702,755 B2
(45) Date of Patent: Apr. 22, 2014

(54) ANGLED WASHER POLYAXIAL CONNECTION FOR DYNAMIC SPINE PROSTHESIS

(75) Inventors: Christopher R. Ralph, Woodinville, WA (US); Cin Kiat Abidin, Issaquah, WA (US); Devin Lee Joseph Looijen, Boulder, CO (US); Matthew M. Quest, Bothell, WA (US); Philip Tracy Berg, Federal Way, WA (US)

(73) Assignee: GMEDELAWARE 2 LLC, Audubon, PA (US)

( * ) Notice: Subject to any disclaimer, the term of this patent is extended or adjusted under 35 U.S.C. 154(b) by 1224 days.

(21) Appl. No.: 11/837,335

(22) Filed: Aug. 10, 2007

(65) Prior Publication Data
US 2008/0103501 A1 May 1, 2008

Related U.S. Application Data

(60) Provisional application No. 60/837,458, filed on Aug. 11, 2006.

(51) Int. Cl.
*A61B 17/58* (2006.01)
*A61F 2/44* (2006.01)

(52) U.S. Cl.
USPC .......................................................... 606/246

(58) Field of Classification Search
USPC ........ 623/17.11–17.16; 606/246–279, 60, 70, 606/71, 280–299, 300–331
See application file for complete search history.

(56) References Cited

U.S. PATENT DOCUMENTS

| 1,308,451 A | 7/1919 | Schachat |
| 2,502,902 A | 4/1950 | Tofflemire |
| 2,930,133 A | 3/1960 | Thompson |
| 2,959,861 A | 11/1960 | Stromquist |
| 3,596,656 A | 8/1971 | Kaute |
| 3,710,789 A | 1/1973 | Ersek |
| 3,726,279 A | 4/1973 | Barefoot et al. |
| 3,867,728 A | 2/1975 | Stubstad et al. |
| 3,875,595 A | 4/1975 | Froning |
| 3,941,127 A | 3/1976 | Froning |

(Continued)

FOREIGN PATENT DOCUMENTS

| DE | 10135771 A1 | 7/2001 |
| DE | 10312755 A1 | 10/2003 |

(Continued)

OTHER PUBLICATIONS

Ochoa et al.; U.S. Appl. No. 12/377,546 entitled "Spinal implant," filed Feb. 13, 2009.

(Continued)

*Primary Examiner* — Christopher Beccia (57) ABSTRACT

A dynamic spine prosthesis (such as a facet joint prosthesis having an articulation surface configured to articulate with a corresponding facet joint element) that has a fixation element with an elongated bone entry portion defining a longitudinal axis and a dynamic spine prosthesis component connected to the fixation element at a connection location by an adjustable connection. The adjustable connection has first and second washers each rotatably supported by the fixation element and each having an angled contact surface in a plane not perpendicular to the longitudinal axis of the fixation element, with the connection location being between the bone entry portion and the first and second washers.

9 Claims, 5 Drawing Sheets (56) References Cited

U.S. PATENT DOCUMENTS

| | | |
|---|---|---|
| 4,040,130 A | 8/1977 | Laure |
| 4,123,848 A | 11/1978 | Emmerich et al. |
| 4,156,296 A | 5/1979 | Johnson et al. |
| 4,210,317 A | 7/1980 | Spann et al. |
| 4,231,121 A | 11/1980 | Lewis |
| 4,271,836 A | 6/1981 | Bacal et al. |
| 4,349,921 A | 9/1982 | Kuntz |
| 4,394,370 A | 7/1983 | Jefferies |
| 4,472,840 A | 9/1984 | Jefferies |
| 4,502,161 A | 3/1985 | Wall |
| 4,554,914 A | 11/1985 | Kapp et al. |
| 4,611,581 A | 9/1986 | Steffee |
| 4,633,722 A | 1/1987 | Beardmore et al. |
| 4,693,722 A | 9/1987 | Wall |
| 4,697,582 A | 10/1987 | William |
| 4,710,075 A | 12/1987 | Davison |
| 4,759,769 A | 7/1988 | Hedman et al. |
| 4,772,287 A | 9/1988 | Ray et al. |
| 4,778,472 A | 10/1988 | Homsy et al. |
| 4,795,469 A | 1/1989 | Oh |
| 4,805,602 A | 2/1989 | Puno et al. |
| 4,863,477 A | 9/1989 | Monson |
| 4,904,260 A | 2/1990 | Ray et al. |
| 4,911,718 A | 3/1990 | Lee et al. |
| 4,917,701 A | 4/1990 | Morgan |
| 4,932,975 A | 6/1990 | Main et al. |
| 4,950,270 A | 8/1990 | Bowman et al. |
| 4,955,916 A | 9/1990 | Carignan et al. |
| 4,957,495 A | 9/1990 | Kluger |
| 4,987,904 A | 1/1991 | Wilson |
| 5,000,165 A | 3/1991 | Watanabe |
| 5,015,255 A | 5/1991 | Kuslich |
| 5,019,081 A | 5/1991 | Watanabe |
| 5,047,055 A | 9/1991 | Bao et al. |
| 5,062,845 A | 11/1991 | Kuslich et al. |
| 5,070,623 A | 12/1991 | Barnes |
| 5,071,437 A | 12/1991 | Steffee |
| 5,092,866 A | 3/1992 | Breard et al. |
| 5,098,434 A | 3/1992 | Serbousek |
| 5,108,399 A | 4/1992 | Eitenmuller et al. |
| 5,129,900 A | 7/1992 | Asher et al. |
| 5,147,404 A | 9/1992 | Downey |
| 5,171,280 A | 12/1992 | Baumgartner |
| 5,192,326 A | 3/1993 | Bao et al. |
| 5,258,031 A | 11/1993 | Salib et al. |
| 5,261,910 A | 11/1993 | Warden et al. |
| 5,284,655 A | 2/1994 | Bogdansky et al. |
| 5,300,073 A | 4/1994 | Ray et al. |
| 5,303,480 A | 4/1994 | Chek |
| 5,306,308 A | 4/1994 | Gross et al. |
| 5,306,309 A | 4/1994 | Wagner et al. |
| 5,312,404 A * | 5/1994 | Asher et al. .............. 606/264 |
| 5,312,409 A | 5/1994 | McLaughlin et al. |
| 5,314,429 A | 5/1994 | Goble |
| 5,314,476 A | 5/1994 | Prewett et al. |
| 5,314,486 A | 5/1994 | Zang et al. |
| 5,314,489 A | 5/1994 | Hoffman et al. |
| 5,314,492 A | 5/1994 | Hamilton et al. |
| 5,329,933 A | 7/1994 | Graf |
| 5,334,203 A | 8/1994 | Wagner |
| 5,348,026 A | 9/1994 | Davidson |
| 5,350,380 A | 9/1994 | Goble et al. |
| 5,360,448 A | 11/1994 | Thramann |
| 5,370,697 A | 12/1994 | Baumgartner |
| 5,401,269 A | 3/1995 | Buttner-Janz et al. |
| 5,405,390 A | 4/1995 | O'Leary et al. |
| 5,413,576 A | 5/1995 | Rivard |
| 5,415,659 A | 5/1995 | Lee et al. |
| 5,415,661 A | 5/1995 | Holmes |
| 5,425,773 A | 6/1995 | Boyd et al. |
| 5,437,669 A | 8/1995 | Yuan et al. |
| 5,437,672 A | 8/1995 | Alleyne |
| 5,443,483 A | 8/1995 | Kirsch |
| 5,445,639 A | 8/1995 | Kuslich et al. |
| 5,458,641 A | 10/1995 | Ramirez Jimenez |
| 5,458,642 A | 10/1995 | Beer et al. |
| 5,458,643 A | 10/1995 | Oka et al. |
| 5,470,333 A | 11/1995 | Ray |
| 5,474,551 A | 12/1995 | Finn et al. |
| 5,474,555 A | 12/1995 | Puno et al. |
| 5,491,882 A | 2/1996 | Walston et al. |
| 5,496,318 A | 3/1996 | Howland et al. |
| 5,501,684 A | 3/1996 | Schlapfer et al. |
| 5,507,823 A | 4/1996 | Walston et al. |
| 5,510,396 A | 4/1996 | Prewett et al. |
| 5,514,180 A | 5/1996 | Heggeness et al. |
| 5,527,312 A | 6/1996 | Ray |
| 5,534,028 A | 7/1996 | Bao et al. |
| 5,534,030 A | 7/1996 | Navarro et al. |
| 5,545,229 A | 8/1996 | Parsons et al. |
| 5,556,431 A | 9/1996 | Buttner-Janz |
| 5,562,738 A | 10/1996 | Boyd et al. |
| 5,569,247 A | 10/1996 | Morrison |
| 5,571,189 A | 11/1996 | Kuslich |
| 5,571,191 A | 11/1996 | Fitz |
| 5,575,792 A | 11/1996 | Errico et al. |
| 5,577,995 A | 11/1996 | Walker et al. |
| 5,587,695 A | 12/1996 | Warmerdam |
| 5,599,311 A | 2/1997 | Raulerson |
| 5,603,713 A | 2/1997 | Aust et al. |
| 5,609,641 A | 3/1997 | Johnson et al. |
| 5,643,263 A | 7/1997 | Simonson |
| 5,645,597 A | 7/1997 | Krapiva |
| 5,645,599 A | 7/1997 | Samani |
| 5,649,930 A | 7/1997 | Kertzner |
| 5,653,762 A | 8/1997 | Pisharodi |
| 5,658,338 A | 8/1997 | Tullos et al. |
| 5,662,651 A | 9/1997 | Tornier et al. |
| 5,672,175 A | 9/1997 | Martin |
| 5,674,295 A | 10/1997 | Ray et al. |
| 5,674,296 A | 10/1997 | Bryan et al. |
| 5,676,701 A | 10/1997 | Yuan et al. |
| 5,678,317 A | 10/1997 | Stefanakos |
| 5,683,391 A | 11/1997 | Boyd |
| 5,683,392 A | 11/1997 | Richelsoph et al. |
| 5,683,464 A | 11/1997 | Wagner et al. |
| 5,683,466 A | 11/1997 | Vitale |
| 5,688,274 A | 11/1997 | Errico et al. |
| 5,690,630 A | 11/1997 | Errico et al. |
| 5,700,268 A | 12/1997 | Bertin |
| 5,702,450 A | 12/1997 | Bisserie |
| 5,704,941 A | 1/1998 | Jacober et al. |
| 5,716,415 A | 2/1998 | Steffee |
| 5,725,527 A | 3/1998 | Biedermann et al. |
| 5,733,284 A | 3/1998 | Martin |
| 5,738,585 A | 4/1998 | Hoyt, III et al. |
| 5,741,255 A | 4/1998 | Krag et al. |
| 5,741,261 A | 4/1998 | Moskovitz et al. |
| 5,766,253 A | 6/1998 | Brosnahan, III |
| 5,776,135 A | 7/1998 | Errico et al. |
| 5,782,833 A | 7/1998 | Haider |
| 5,797,911 A | 8/1998 | Sherman et al. |
| 5,800,433 A | 9/1998 | Benzel et al. |
| 5,824,093 A | 10/1998 | Ray et al. |
| 5,824,094 A | 10/1998 | Serhan et al. |
| 5,827,289 A | 10/1998 | Reiley et al. |
| 5,836,948 A | 11/1998 | Zucherman et al. |
| 5,860,977 A | 1/1999 | Zucherman et al. |
| 5,863,293 A | 1/1999 | Richelsoph |
| 5,865,846 A | 2/1999 | Bryan et al. |
| 5,866,113 A | 2/1999 | Hendriks et al. |
| 5,868,745 A | 2/1999 | Alleyne |
| 5,879,350 A | 3/1999 | Sherman et al. |
| 5,879,396 A | 3/1999 | Walston et al. |
| 5,885,285 A | 3/1999 | Simonson |
| 5,885,286 A | 3/1999 | Sherman et al. |
| 5,891,145 A | 4/1999 | Morrison et al. |
| 5,893,889 A | 4/1999 | Harrington |
| RE36,221 E | 6/1999 | Breard et al. |
| 5,947,893 A | 9/1999 | Agrawal et al. |
| 5,947,965 A | 9/1999 | Bryan |
| 5,964,760 A | 10/1999 | Richelsoph |
| 5,984,924 A * | 11/1999 | Asher et al. .............. 606/264 |
| 5,984,926 A | 11/1999 | Jones |

(56) References Cited

U.S. PATENT DOCUMENTS

| | | |
|---|---|---|
| 6,001,130 A | 12/1999 | Bryan et al. |
| 6,004,353 A | 12/1999 | Masini |
| 6,010,503 A | 1/2000 | Richelsoph et al. |
| 6,014,588 A | 1/2000 | Fitz |
| 6,019,759 A | 2/2000 | Rogozinski |
| 6,019,792 A | 2/2000 | Cauthen |
| 6,022,350 A | 2/2000 | Ganem |
| 6,039,763 A | 3/2000 | Shelokov |
| 6,048,342 A | 4/2000 | Zucherman et al. |
| 6,050,997 A | 4/2000 | Mullane |
| 6,053,917 A | 4/2000 | Sherman et al. |
| 6,063,121 A | 5/2000 | Xavier et al. |
| 6,066,325 A | 5/2000 | Wallace et al. |
| 6,068,630 A | 5/2000 | Zuckerman et al. |
| RE36,758 E | 6/2000 | Fitz |
| 6,074,391 A | 6/2000 | Metz-Stavenhagen et al. |
| 6,077,262 A | 6/2000 | Schläpfer et al. |
| 6,080,157 A | 6/2000 | Cathro et al. |
| 6,086,590 A | 7/2000 | Margulies et al. |
| 6,090,111 A | 7/2000 | Nichols |
| 6,113,600 A | 9/2000 | Drummond et al. |
| 6,113,637 A | 9/2000 | Gill et al. |
| 6,120,510 A | 9/2000 | Albrektsson et al. |
| 6,132,430 A | 10/2000 | Wagner |
| 6,132,462 A | 10/2000 | Li |
| 6,132,464 A | 10/2000 | Martin |
| 6,132,465 A | 10/2000 | Ray et al. |
| 6,165,177 A | 12/2000 | Wilson et al. |
| 6,190,388 B1 | 2/2001 | Michelson et al. |
| 6,193,724 B1 | 2/2001 | Chan |
| 6,193,758 B1 | 2/2001 | Huebner |
| 6,200,322 B1 | 3/2001 | Branch et al. |
| 6,214,012 B1 | 4/2001 | Karpman et al. |
| 6,224,602 B1 | 5/2001 | Hayes |
| 6,231,575 B1 | 5/2001 | Krag |
| 6,248,105 B1 | 6/2001 | Schläpfer et al. |
| 6,280,443 B1 | 8/2001 | Gu et al. |
| 6,290,703 B1 | 9/2001 | Ganem |
| 6,293,949 B1 | 9/2001 | Justis et al. |
| 6,302,890 B1 | 10/2001 | Leone, Jr. |
| 6,309,391 B1 | 10/2001 | Crandall et al. |
| 6,312,431 B1 | 11/2001 | Asfora |
| 6,340,361 B1 | 1/2002 | Kraus et al. |
| 6,340,477 B1 | 1/2002 | Anderson |
| 6,342,054 B1 | 1/2002 | Mata |
| 6,361,506 B1 | 3/2002 | Saenger et al. |
| 6,368,320 B1 | 4/2002 | Le Couedic et al. |
| 6,419,703 B1 | 7/2002 | Fallin et al. |
| 6,440,169 B1 | 8/2002 | Elberg et al. |
| 6,443,954 B1 | 9/2002 | Bramlet et al. |
| 6,451,021 B1 | 9/2002 | Ralph et al. |
| 6,471,705 B1 | 10/2002 | Biedermann et al. |
| 6,514,253 B1 | 2/2003 | Yao |
| 6,520,963 B1 | 2/2003 | McKinley |
| 6,524,315 B1 | 2/2003 | Selvitelli et al. |
| 6,540,749 B2 | 4/2003 | Schäfer et al. |
| 6,547,790 B2 | 4/2003 | Harkey, III et al. |
| 6,554,843 B1 | 4/2003 | Ou |
| 6,565,565 B1 | 5/2003 | Yuan et al. |
| 6,565,572 B2 | 5/2003 | Chappius |
| 6,565,605 B2 | 5/2003 | Goble et al. |
| 6,572,617 B1 | 6/2003 | Senegas |
| 6,579,319 B2 | 6/2003 | Goble et al. |
| 6,585,740 B2 | 7/2003 | Schlapfer et al. |
| 6,585,769 B1 | 7/2003 | Muhanna et al. |
| 6,607,530 B1 | 8/2003 | Carl et al. |
| 6,610,091 B1 | 8/2003 | Reiley |
| 6,619,091 B2 | 9/2003 | Heffe |
| 6,623,485 B2 | 9/2003 | Doubler et al. |
| 6,626,909 B2 | 9/2003 | Chin |
| 6,632,226 B2 | 10/2003 | Chan |
| 6,638,281 B2 | 10/2003 | Gorek |
| 6,645,214 B2 | 11/2003 | Brown et al. |
| 6,648,891 B2 | 11/2003 | Kim |
| 6,669,697 B1 * | 12/2003 | Pisharodi ............... 606/264 |
| 6,669,698 B1 | 12/2003 | Tromanhauser et al. |
| 6,669,729 B2 | 12/2003 | Chin |
| 6,712,818 B1 | 3/2004 | Michelson |
| 6,712,849 B2 | 3/2004 | Re et al. |
| 6,736,815 B2 | 5/2004 | Ginn |
| 6,749,361 B2 | 6/2004 | Hermann et al. |
| 6,761,698 B2 | 7/2004 | Shibata et al. |
| 6,761,720 B1 | 7/2004 | Senegas |
| 6,770,095 B2 | 8/2004 | Grinberg et al. |
| 6,783,527 B2 | 8/2004 | Drewry et al. |
| 6,790,233 B2 | 9/2004 | Brodke et al. |
| 6,793,678 B2 | 9/2004 | Hawkins |
| 6,802,844 B2 | 10/2004 | Ferree |
| 6,811,567 B2 | 11/2004 | Reiley |
| 6,902,567 B2 | 6/2005 | Del Medico |
| 6,902,580 B2 | 6/2005 | Fallin et al. |
| 6,908,465 B2 | 6/2005 | von Hoffmann et al. |
| 6,949,123 B2 | 9/2005 | Reiley |
| 6,974,478 B2 | 12/2005 | Reiley |
| 6,979,299 B2 | 12/2005 | Peabody et al. |
| 7,011,658 B2 | 3/2006 | Young |
| 7,044,969 B2 | 5/2006 | Errico et al. |
| 7,051,451 B2 | 5/2006 | Augostino et al. |
| 7,220,262 B1 | 5/2007 | Hynes |
| 7,294,127 B2 | 11/2007 | Leung et al. |
| 7,302,288 B1 | 11/2007 | Schellenberg |
| 7,309,338 B2 | 12/2007 | Cragg |
| 7,445,635 B2 | 11/2008 | Fallin et al. |
| 7,455,685 B2 | 11/2008 | Justis |
| 7,547,324 B2 | 6/2009 | Cragg et al. |
| 7,608,104 B2 * | 10/2009 | Yuan et al. ............... 623/17.11 |
| 7,766,943 B1 * | 8/2010 | Fallin et al. ............... 606/264 |
| 7,799,054 B2 * | 9/2010 | Kwak et al. ............... 606/246 |
| 2001/0012938 A1 | 8/2001 | Zucherman et al. |
| 2001/0020170 A1 | 9/2001 | Zucherman et al. |
| 2002/0013585 A1 | 1/2002 | Gournay et al. |
| 2002/0013588 A1 | 1/2002 | Landry et al. |
| 2002/0029039 A1 | 3/2002 | Zucherman et al. |
| 2002/0042613 A1 | 4/2002 | Mata |
| 2002/0049446 A1 | 4/2002 | Harkey, III et al. |
| 2002/0052603 A1 | 5/2002 | Nickols et al. |
| 2002/0065557 A1 | 5/2002 | Goble et al. |
| 2002/0068975 A1 | 6/2002 | Teitelbaum et al. |
| 2002/0082601 A1 | 6/2002 | Toyama et al. |
| 2002/0120272 A1 | 8/2002 | Yuan et al. |
| 2002/0123752 A1 | 9/2002 | Schultheiss et al. |
| 2002/0123806 A1 | 9/2002 | Reiley |
| 2002/0151895 A1 | 10/2002 | Soboleski et al. |
| 2003/0004572 A1 | 1/2003 | Goble et al. |
| 2003/0028250 A1 | 2/2003 | Reiley et al. |
| 2003/0040797 A1 | 2/2003 | Fallin et al. |
| 2003/0055427 A1 | 3/2003 | Graf |
| 2003/0069603 A1 | 4/2003 | Little et al. |
| 2003/0125740 A1 | 7/2003 | Khanna |
| 2003/0181914 A1 | 9/2003 | Johnson et al. |
| 2003/0191532 A1 | 10/2003 | Goble et al. |
| 2003/0195631 A1 | 10/2003 | Ferree |
| 2003/0204259 A1 | 10/2003 | Goble et al. |
| 2003/0204261 A1 | 10/2003 | Eisermann et al. |
| 2003/0233148 A1 | 12/2003 | Ferree |
| 2004/0006391 A1 | 1/2004 | Reiley |
| 2004/0049205 A1 | 3/2004 | Lee et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049281 A1 | 3/2004 | Reiley |
| 2004/0059429 A1 | 3/2004 | Amin et al. |
| 2004/0111154 A1 | 6/2004 | Reiley |
| 2004/0116927 A1 | 6/2004 | Graf |
| 2004/0127989 A1 | 7/2004 | Dooris et al. |
| 2004/0143264 A1 | 7/2004 | McAfee |
| 2004/0204710 A1 | 10/2004 | Patel et al. |
| 2004/0204718 A1 | 10/2004 | Hoffman |
| 2004/0230201 A1 | 11/2004 | Yuan et al. |
| 2004/0230304 A1 | 11/2004 | Yuan et al. |

(56) References Cited

U.S. PATENT DOCUMENTS

| | | |
|---|---|---|
| 2004/0260305 A1 | 12/2004 | Gorensek et al. |
| 2004/0267279 A1 | 12/2004 | Casutt et al. |
| 2005/0010291 A1 | 1/2005 | Stinson et al. |
| 2005/0015146 A1 | 1/2005 | Louis et al. |
| 2005/0027359 A1 | 2/2005 | Mashburn |
| 2005/0027361 A1 | 2/2005 | Reiley |
| 2005/0033431 A1 | 2/2005 | Gordon et al. |
| 2005/0033432 A1 | 2/2005 | Gordon et al. |
| 2005/0033434 A1 | 2/2005 | Berry |
| 2005/0033439 A1 | 2/2005 | Gordon et al. |
| 2005/0043799 A1 | 2/2005 | Reiley |
| 2005/0049705 A1 | 3/2005 | Hale et al. |
| 2005/0055096 A1 | 3/2005 | Serhan et al. |
| 2005/0059972 A1 | 3/2005 | Biscup |
| 2005/0080428 A1 | 4/2005 | White |
| 2005/0080486 A1 | 4/2005 | Fallin et al. |
| 2005/0085912 A1 | 4/2005 | Arnin et al. |
| 2005/0101956 A1 | 5/2005 | Simonson |
| 2005/0102028 A1 | 5/2005 | Arnin et al. |
| 2005/0119748 A1 | 6/2005 | Reiley et al. |
| 2005/0131406 A1 | 6/2005 | Reiley et al. |
| 2005/0131409 A1 | 6/2005 | Chervitz et al. |
| 2005/0131537 A1 | 6/2005 | Hoy et al. |
| 2005/0131538 A1 | 6/2005 | Chervitz et al. |
| 2005/0131545 A1 | 6/2005 | Chervitz et al. |
| 2005/0137705 A1 | 6/2005 | Reiley |
| 2005/0137706 A1 | 6/2005 | Reiley |
| 2005/0143818 A1 | 6/2005 | Yuan et al. |
| 2005/0149190 A1 | 7/2005 | Reiley |
| 2005/0159746 A1 | 7/2005 | Grob et al. |
| 2005/0165484 A1 | 7/2005 | Ferree et al. |
| 2005/0177240 A1 | 8/2005 | Blain |
| 2005/0187560 A1 | 8/2005 | Dietzel et al. |
| 2005/0192589 A1 | 9/2005 | Raymond et al. |
| 2005/0203533 A1 | 9/2005 | Ferguson et al. |
| 2005/0222683 A1 | 10/2005 | Berry |
| 2005/0228500 A1 | 10/2005 | Kim et al. |
| 2005/0234459 A1* | 10/2005 | Falahee et al. ................ 606/72 |
| 2005/0234552 A1 | 10/2005 | Reiley |
| 2005/0240264 A1 | 10/2005 | Tokish, Jr. et al. |
| 2005/0240265 A1 | 10/2005 | Kuiper et al. |
| 2005/0240266 A1 | 10/2005 | Kuiper et al. |
| 2005/0251256 A1 | 11/2005 | Reiley |
| 2005/0261770 A1 | 11/2005 | Kuiper et al. |
| 2005/0267579 A1 | 12/2005 | Reiley et al. |
| 2005/0273167 A1 | 12/2005 | Triplett et al. |
| 2005/0277922 A1 | 12/2005 | Trieu et al. |
| 2005/0283238 A1 | 12/2005 | Reiley |
| 2006/0007562 A1* | 1/2006 | Willey et al. ................. 359/811 |
| 2006/0009847 A1 | 1/2006 | Reiley |
| 2006/0009848 A1 | 1/2006 | Reiley |
| 2006/0009849 A1 | 1/2006 | Reiley |
| 2006/0025769 A1 | 2/2006 | Dick et al. |
| 2006/0029186 A1 | 2/2006 | De Villiers et al. |
| 2006/0036246 A1 | 2/2006 | Carl et al. |
| 2006/0041311 A1 | 2/2006 | McLeer |
| 2006/0041314 A1 | 2/2006 | Millard |
| 2006/0052785 A1 | 3/2006 | Augostino et al. |
| 2006/0058790 A1 | 3/2006 | Carl et al. |
| 2006/0058791 A1 | 3/2006 | Broman et al. |
| 2006/0079895 A1 | 4/2006 | McLeer |
| 2006/0085010 A1 | 4/2006 | Lieberman |
| 2006/0085072 A1 | 4/2006 | Funk et al. |
| 2006/0085075 A1 | 4/2006 | McLeer |
| 2006/0100707 A1 | 5/2006 | Stinson et al. |
| 2006/0100709 A1 | 5/2006 | Reiley et al. |
| 2006/0106398 A1 | 5/2006 | Lauryssen et al. |
| 2006/0122703 A1 | 6/2006 | Aebi et al. |
| 2006/0149375 A1 | 7/2006 | Yuan et al. |
| 2006/0184180 A1 | 8/2006 | Augostino et al. |
| 2006/0241532 A1 | 10/2006 | Murakami et al. |
| 2006/0265070 A1 | 11/2006 | Stinson et al. |
| 2006/0271046 A1* | 11/2006 | Kwak et al. ................. 606/61 |
| 2007/0079517 A1 | 4/2007 | Augostino et al. |
| 2007/0088358 A1 | 4/2007 | Yuan et al. |
| 2007/0093833 A1 | 4/2007 | Kuiper et al. |
| 2007/0168029 A1 | 7/2007 | Yuan et al. |
| 2007/0233256 A1 | 10/2007 | Ohrt et al. |
| 2007/0239159 A1 | 10/2007 | Altarac et al. |
| 2007/0255411 A1 | 11/2007 | Reiley |
| 2007/0265706 A1 | 11/2007 | Reiley et al. |
| 2007/0276370 A1 | 11/2007 | Altarac et al. |
| 2007/0276374 A1 | 11/2007 | Broman et al. |
| 2007/0282344 A1 | 12/2007 | Yedlicka et al. |
| 2007/0282445 A1 | 12/2007 | Reiley |
| 2008/0015583 A1 | 1/2008 | Reiley |
| 2008/0015696 A1 | 1/2008 | Reiley |
| 2008/0039866 A1 | 2/2008 | Stetz et al. |
| 2009/036925 A1 | 2/2009 | Sala et al. |

FOREIGN PATENT DOCUMENTS

| | | |
|---|---|---|
| EP | 1103226 | 5/2001 |
| EP | 1205152 A1 | 5/2002 |
| EP | 1254639 A1 | 11/2002 |
| FR | 2726459 | 5/1996 |
| FR | 2749155 | 12/1997 |
| FR | 2844180 | 3/2004 |
| IE | S970323 | 6/1998 |
| JP | 59010807 A | 1/1984 |
| JP | 10082605 A | 3/1998 |
| JP | 10179622 A | 7/1998 |
| WO | WO 95/05783 A1 | 3/1995 |
| WO | WO 96/00049 A1 | 1/1996 |
| WO | WO 98/48717 A1 | 11/1998 |
| WO | WO 98/56301 A1 | 12/1998 |
| WO | WO 99/05995 A1 | 2/1999 |
| WO | WO 99/23963 A1 | 5/1999 |
| WO | WO 99/60957 A1 | 12/1999 |
| WO | WO 99/65412 A1 | 12/1999 |
| WO | WO 00/38582 A1 | 7/2000 |
| WO | WO 00/62684 A1 | 10/2000 |
| WO | WO 01/06939 A1 | 2/2001 |
| WO | WO 01/15638 A1 | 3/2001 |
| WO | WO 01/28442 A1 | 4/2001 |
| WO | WO 01/30248 A1 | 5/2001 |
| WO | WO 01/39678 A1 | 6/2001 |
| WO | WO 01/67972 A2 | 9/2001 |
| WO | WO 01/97721 A2 | 12/2001 |
| WO | WO 02/00270 A1 | 1/2002 |
| WO | WO 02/00275 A1 | 1/2002 |
| WO | WO 02/02024 A1 | 1/2002 |
| WO | WO 02/02158 A1 | 1/2002 |
| WO | WO 02/34150 A2 | 5/2002 |
| WO | WO 02/43603 A1 | 6/2002 |
| WO | WO 02/071960 A2 | 9/2002 |
| WO | WO 02/089712 A1 | 11/2002 |
| WO | WO 03/020143 A1 | 3/2003 |
| WO | WO 03/041618 A2 | 5/2003 |
| WO | WO 03/075805 A1 | 9/2003 |
| WO | WO 03/101350 A1 | 12/2003 |
| WO | WO 2004/071358 A1 | 8/2004 |
| WO | WO 2004/103227 A1 | 12/2004 |
| WO | WO 2004/103228 A1 | 12/2004 |
| WO | WO 2005/009301 A1 | 2/2005 |
| WO | WO 2005/079711 A1 | 9/2005 |

OTHER PUBLICATIONS

Hewko, Brian; U.S. Appl. No. 12/377,552 entitled "Spinal implant," filed Feb. 13, 2009.

Quest et al.; U.S. Appl. No. 12/099,068 entitled "Measurement and trialing system and methods for orthopedic device component selection," filed Apr. 7, 2008.

Reiley, Mark; U.S. Appl. No. 12/176,280 entitled "Facet arthroplasty devices and methods," filed Jul. 18, 2008.

Yuan et al; U.S. Appl. No. 12/163,738 entitled "Prostheses, tools and methods for replacement of natural joints with artificial facet joint surfaces," filed Jun. 27, 2008.

Funk et al; U.S. Appl. No. 12/186,461 entitled "Implantable orthopedic device component selection instrument and methods," filed Aug. 5, 2008.

(56) References Cited

OTHER PUBLICATIONS

Yuan et al.; U.S. Appl. No. 12/027,899 entitled "Prostheses, tools and methods for replacement of natural facet joints with artificial facet joint surfaces," filed Feb. 7, 2008.
Reiley et al; U.S. Appl. No. 12/058,403 entitled "Polyaxial adjustment of facet joint prostheses," filed Mar. 28, 2008.
Abraham, D.J. et al. "Indications and Trends in Use in Cervical Spinal Fusions." Orthop Clin North Am. Oct. 1998; 29(4):731-44.
Eichholz, K.M. et al. "Complications of Revision Spinal Surgery", Neurosurg Focus; (Sep. 15, 2003), 15(3): pp. 1-4.
Farfan, H.F. Effects of Torsion on the Intervertebral Joints. The Canadian Journal of Surgery, Jul. 1969; 12(3):336-41.
Farfan, H.F. et al. "The Relation of Facet Orientation to Intervertebral Disc Failure." The Canadian Journal of Surgery, Apr. 1967; 10(2):179-85.
Farfan, H.F. The Pathological Anatomy of Degenerative Spondylolisthesis. A Cadaver Study. Spine. Sep.-Oct. 1980; 5(5):412-8.
Fosbinder, R.A. et al. Essentials of Radiologic Science. The McGraw-Hill Companies; 2002.
Goh, J.C. et al. "Influence of PLIF cage size on lumbar spine stability." Spine. Jan. 2000, 25(1) Medline abstract (one page).
Guyer R. et al. "Impliant: Motion Preservation through Total Posterior-Element Replacement." May 7, 2004 Presentation held at Hofburg Center, Vienna, Austria, (2 pages).
Head, W.C. "Wagner surface replacement arthroplasty of the hip." Analysis of fourteen failures in forty-one hips. J Bone Joint Surg. Am; Mar. 1981, 63(3), Medline abstract (one page).
Khoo, L.T. et al. "A biomechanical analysis of the effects of lumbar fusion on the adjacent vetebral motion segment." Proceedings of the 2000 Annual Meeting of the North American Spine Society, New Orleans, pp. 127-128.
Kirkaldy-Willis, W.H. et al. "Pathology and Pathogenesis of Lumbar Spondylosis and Stenosis." Spine. Dec. 1978; 3(4):319-28.
Kotani, Y. et al. The effects of spinal fixation and destabilization on the biomechanical and histologic properties of spinal ligaments. An in vivo study. Spine, Mar. 15, 1998, 23(6), Medline abstract (2 pages).
Kulkarni, et al. "Accelerated Spondylotic Changes Adjacent to the Fused Segment Following Central Cervical Corpectomy: Magnetic Resonance Imaging Study Evidence." J. Neurosurg (Spine 1). 2004; 100: 2-6.
Lam, K. N., et al. X-ray "Diagnosis: A Physician's Approach." Springer-Verlag; 1998.
Lemaire, J.P. et al. "Intervertebral disc prosthesis: results and prospects for the year 2000." Clinical Orthopaedics and Related Research. 1997; No. 337, pp. 64-76.
Lombardi, J.S. et al. "Treatment of Degenerative Spondylolisthesis." Spine. 1985; 10(9): 821-7.
McMillin, C. R. et al. Artificial Spinal Discs with up to Five Years Follow-up. 20th Annual Meeting of the Society for Biomaterials (Abstract) 1994; p. 89.
Nagata, H. et al. "The effects of immobilization of long segments of the spine on the adjacent and distal facet force and lumbrosacral motion". Spine, Dec. 1993; 18(16):2471-2479, (9 pages).
Nibu, K. et al. "Multidirectional stabilizing potential of BAK interbody spinal fusion system for anterior surgery." J Spinal Discord, Aug. 1997; 10(4), Medline abstract (one page).
Posner, I. et al. A "Biomechanical Analysis of the Clinical Stability of the Lumbar and Lumbosacral Spine." Spine. 1982; 7(4): 374-389.
Rosenberg, N. J. "Degenerative Spondylolisthesis. Predisposing Factors." The Journal of Bone and Joint Surgery. 1975; 57-A(4): 467-74.
Sacher, R., Impliant Brochure for presentation at MedTech Insight Conference (Oct. 31, 2003) Boston, MA. pp. 93-94.
Slone, R. M. et al. Body CT: A Practical Approach. The McGraw-Hill Companies; 1999.
Stout, G. H. et al. X-Ray Structure Determination: A Practical Guide. 2nd Edition. John Wiley & Sons; 1989.
Szpalski, M., et al. Spine Arthroplasty: A Historical Review. Eur Spine J. 2002; 11(Suppl. 2): S65-S84.

Tsantrizos, A. et al. "Segmental stability and compressive strength of posterior lumbar interbody fusion implants." Spine, Aug. 1, 2000; 25(15), Medline abstract (one page).
UCR Pedicle Screw System from SeaSpine (information available at http://www.seaspine.com/UCR_Pedicle_Screw_System.html). Accessed Dec. 5, 2005.
Victrex of Lancashire, Great Britain. (information on Victrex available at http://www.matweb.com). Accessed Dec. 5, 2005.
Berg, et al; U.S. Appl. No. 11/800,895 entitled "Minimally Invasive Spine Restoration Systems, Devices, Methods, and Kits," filed May 7, 2007.
Reiley et al; U.S. Appl. No. 11/577,872 entitled "Facet Joint Prosthesis" which entered the U.S. from the National Phase Apr. 24, 2007.
Reiley et al; U.S. Appl. No. 11/577,923 entitled "Facet Joint Prostheses" filed Apr. 25, 2007.
Kuiper et al; U.S. Appl. No. 11/577,964 entitled "Crossbar Spinal Prosthesis Having a Modular Design and Systems for Treating Spinal Pathologies," filed Apr. 25, 2007.
Kuiper et al; U.S. Appl. No. 11/577,967 entitled "Crossbar Spinal Prosthesis having a Modular Design and Systems for Treating Spinal Pathologies," filed Apr. 25, 2007.
Reiley, Mark; U.S. Appl. No. 11/831,870 entitled "Prostheses systems and methods for replacement of natural facet joints with artificial facet joint surfaces," filed Jul. 31, 2007.
Stone et al; U.S. Appl. No. 11/861,239 entitled "Facet Replacement Device Removal and Revision Systems and Methods" filed Sep. 25, 2007.
McLeer, Thomas, U.S. Appl. No. 11/934,724 entitled "Polymeric Joint Complex and Methods of Use" filed Nov. 2, 2007.
McLeer, Thomas, U.S. Appl. No. 11/934,720 entitled "Polymeric Joint Complex and Methods of Use" filed Nov. 2, 2007.
McLeer, Thomas, U.S. Appl. No. 11/934,719 entitled "Polymeric Joint Complex and Methods of Use" filed Nov. 2, 2007.
Reiley, Mark, U.S. Appl. No. 11/934,713 entitled "Facet arthroplasty devices and methods" filed Nov. 2, 2007.
Reiley, Mark, U.S. Appl. No. 11/939,540 entitled "Facet arthroplasty devices and methods" filed Nov. 13, 2007.
Reiley, Mark, U.S. Appl. No. 11/943,458 entitled "Facet arthroplasty devices and methods" filed Nov. 20, 2007.
Reiley, Mark, U.S. Appl. No. 11/949,007 entitled "Facet arthroplasty devices and methods" filed Nov. 30, 2007.
Reiley, Mark, U.S. Appl. No. 11/949,000 entitled "Facet arthroplasty devices and methods" filed Nov. 30, 2007.
Reiley et al.; U.S. Appl. No. 11/948,963 entitled "Prostheses, systems and methods for replacement of natural facet joints with artificial facet joint surfaces" filed Nov. 30, 2007.
Reiley, Mark, U.S. Appl. No. 11/957,208 entitled "Facet arthroplasty devices and methods" filed Dec. 14, 2007.
Reiley et al.; U.S. Appl. No. 11/957,315 entitled "Prostheses, systems and methods for replacement of natural facet joints with artificial facet joint surfaces" filed Dec. 14, 2007.
Reiley, Mark; U.S. Appl. No. 11/957,175 entitled "Facet arthroplasty devices and methods" filed Dec. 14, 2007.
Reiley et al.; U.S. Appl. No. 11/957,290 entitled "Prostheses, systems and methods for replacement of natural facet joints with artificial facet joint surfaces" filed Dec. 14, 2007.
Reiley, Mark; U.S. Appl. No. 11/956,961 entitled "Facet arthroplasty devices and methods" filed Dec. 14, 2007.
Reiley, Mark; U.S. Appl. No. 11/957,149 entitled "Facet arthroplasty devices and methods" filed Dec. 14, 2007.
Reiley, Mark; U.S. Appl. No. 11/957,061 entitled "Facet arthroplasty devices and methods" filed Dec. 14, 2007.
Reiley et al.; U.S. Appl. No. 11/957,259 entitled "Prostheses, systems and methods for replacement of natural facet joints with artificial facet joint surfaces" filed Dec. 14, 2007.
Reiley, Mark; U.S. Appl. No. 12/016,177 entitled "Facet arthroplasty devices and methods" filed Jan. 17, 2008.
Kuiper et al.; U.S. Appl. No. 11/948,994 entitled "Crossbar spinal prosthesis having a modular design and related implantation methods" filed Nov. 30, 2007.

(56) References Cited

OTHER PUBLICATIONS

Kuiper et al.; U.S. Appl. No. 11/948,973 entitled "Crossbar spinal prosthesis having a modular design and related implantation methods" filed Nov. 30, 2007.

Kuiper et al.; U.S. Appl. No. 11/957,303 entitled "Crossbar spinal prosthesis having a modular design and related implantation methods" filed Nov. 30, 2007.

McLeer, Thomas; U.S. Appl. No. 11/952,988 entitled "Polymeric joint complex and methods of use" filed Dec. 7, 2007.

* cited by examiner

ANGLED WASHER POLYAXIAL CONNECTION FOR DYNAMIC SPINE PROSTHESIS

CROSS REFERENCE TO RELATED APPLICATIONS

This application claims the benefit under 35 U.S.C. § 119 of U.S. Provisional Application No. 60/837,458 filed Aug. 11, 2006, which application is incorporated by reference as if fully set forth herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

The invention relates generally to dynamic spine prostheses. In particular, the invention relates to dynamic spine prostheses with components whose position with respect to a spine fixation element may be adjusted.

There are multiple types of spine modification devices that may be implanted by attachment to one or more vertebrae to treat a variety of disorders. For example, spinal fusion systems fix the spatial relationships between two or more vertebrae. One such system is described in U.S. Pat. No. 6,080,156. Fusion systems, such as the one shown in the '156 patent, are typically attached to the vertebrae by screws placed in the pedicle. Because all components of such fusion systems are essentially immobile with respect to each other, each component must continually bear and transmit to adjacent components all forces exerted on the device anywhere in the device until the treated vertebral bodies have fused, at which point the bony fusion generally absorbs the majority of the intervertebral loads. Because such fusion devices are typically utilized in conjunction with other fusion-promoting techniques and tools, such as disc evacuation and packing with bone graft, the use of interbody fusion cages and bone graft, gutter grafting and/or the use of BMP or other arthrodesis promoting tools and techniques, it is generally only necessary for such fusion devices to function for a limited amount of time before the arthrodesis assumes the majority of the vertebral loading.

Unlike fusion systems, however, dynamic spine prostheses attach to two or more vertebrae and have components that move with respect to each other as the vertebrae to which they are attached move. Moreover, dynamic spine prostheses should be designed to assume normal physiological loading (as well as transient excessive loading conditions) for the lifetime of the patient, which could easily exceed 10,000,000 cycles or more. Dynamic spine prostheses can include artificial facet joint prostheses (such as, e.g., the Total Facet Arthroplasty System® available from Archus Orthopedics, Inc., the AFRS system available from Facet Solutions, and the TOPS system available from Impliant, Ltd.) as well as dynamic stabilization systems (such as, e.g., the Stabilimax NZ system available from Applied Spine Technologies, the Axient system available from Innovative Spinal Technologies, the N-Flex system available from N-Spine, and the Accuflex system available from Globus Medical.) and dynamic interspinous-spacer systems (such as, e.g., the X-Stop system available from Kyphon/St. Francis Medical Technologies, the Coflex system available from Paradigm Spine, the Extensure system available from Nuvasive, and the Wallis system available from Abbott Spine.).

SUMMARY OF THE INVENTION

Due to patient to patient differences in spinal anatomy as well as to anatomical changes caused by a particular patient's disease state, the relationship between the fixation elements (such as screws, posts, etc.) of a dynamic spine prosthesis to the remaining components of the prosthesis may vary from patient to patient and from disease state to disease state. However, unlike spinal fusion prosthesis, the connections between the fixation elements and the dynamic (or motion-allowing) elements of a dynamic spine prosthesis must be capable of withstanding repetitive loading (both normal physiological loading as well as transient excessive loading) for the remaining lifetime of the patient. The invention therefore provides an adjustable connection between a dynamic spine prosthesis fixation element and other components of the prosthesis which is capable of withstanding such loading for an extended period of time, up to, and including, the lifetime of the patient and/or the implant. Moreover, because physicians will also often desire the fixation elements to be placed in a desired location and/or orientation relative to the surrounding anatomical structures (such as to increase the strength of the of the fixation by maximizing cortical bone purchase and/or to accommodate unusual or size-constrained anatomical features), and such positioning is often non-optimal for the placement of the dynamic elements of the device, the present invention allows the physician to place the fixation elements in virtually any orientation or position, and then securely fix the properly-functioning implant relative to the location and/or orientation of the fixation members.

The invention relates generally to implantable devices, apparatus or mechanisms that are suitable for implantation within a human body to restore, augment, and/or replace hard tissue, soft tissue and/or connective tissue, including bone and cartilage, and systems for treating the anatomic or functional manifestation of injury or diseases, such as spinal pathologies. In some instances, the implantable devices can include devices designed to replace missing, removed, or resected body parts or structure. The implantable devices, apparatus or mechanisms are configured such that the devices can be formed from parts, elements or components which alone or in combination comprise the device. The implantable devices can also be configured such that one or more elements or components are formed integrally to achieve a desired physiological, operational or functional result such that the components complete the device. Functional results can include the surgical restoration and functional power of a joint, controlling, limiting or altering the functional power of a joint, and/or eliminating the functional power of a joint by preventing joint motion. Portions of the device can be configured to replace or augment existing anatomy and/or implanted devices, and/or be used in combination with resection or removal of existing anatomical structure.

One aspect of the invention provides a dynamic spine prosthesis (such as, for example, a facet joint prosthesis having an articulation surface configured to articulate with a corresponding facet joint element) that has a fixation element with an elongated bone entry portion defining a longitudinal axis and a dynamic spine prosthesis component connected to the fixation element at a connection location by an adjustable connection. The adjustable connection has first and second washers each rotatably supported by the fixation element and each having an angled contact surface in a plane not perpendicular to the longitudinal axis of the fixation element, with the connection location being between the bone entry portion and the first and second washers.

In some embodiments, the angled contact surfaces of the first and second washers are in contact with each other. There also may be a third washer between the dynamic spine prosthesis connection location and the bone entry portion, with the third washer comprising a partial spherical surface.

In some embodiments, the dynamic spine prosthesis also has a tightening element (such as, e.g., a compression nut) having a first position enabling movement between the first and second washers and the fixation element and a second position preventing movement between the washers and the fixation element.

In some embodiments, the adjustable connection also has a structural attachment element supporting the dynamic spine prosthesis component, with the structural attachment element having a first position in which the dynamic spine prosthesis component is movable with respect to the structural element and a second position in which the dynamic spine prosthesis component is fixed with respect to the structural element.

Another aspect of the invention provides a method of adjusting a position of a component of a dynamic spine prosthesis (such as a facet joint prosthesis having an articulation surface configured to articulate with a corresponding facet joint element) with respect to a bone fixation element supporting the dynamic spine prosthesis. The method includes the steps of inserting a bone entry portion of the fixation element into a vertebra; moving the dynamic spine prosthesis component to a desired position with respect to a connection location between the dynamic spine prosthesis component and the fixation element, the connection location being between the bone entry portion and first and second washers, the first and second washers each having an angled contact surface in a plane not perpendicular to a longitudinal axis of the fixation element and being supported by the fixation element; rotating the first washer with respect to the second washer; and immobilizing the washers and the dynamic spine prosthesis component with respect to the fixation element.

In some embodiments, the method includes the step of rotating the second washer with respect to the fixation element.

In some embodiments, the step of moving the dynamic spine prosthesis component includes the step of moving the dynamic spine prosthesis component with respect to a support disposed at the connection location. In some embodiments, the immobilizing step may include the step of immobilizing the dynamic spine prosthesis component with respect to the support, such as by tightening a compression nut threadably mounted on an extension of the fixation element.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which.

DETAILED DESCRIPTION OF THE INVENTION

Figure 1:
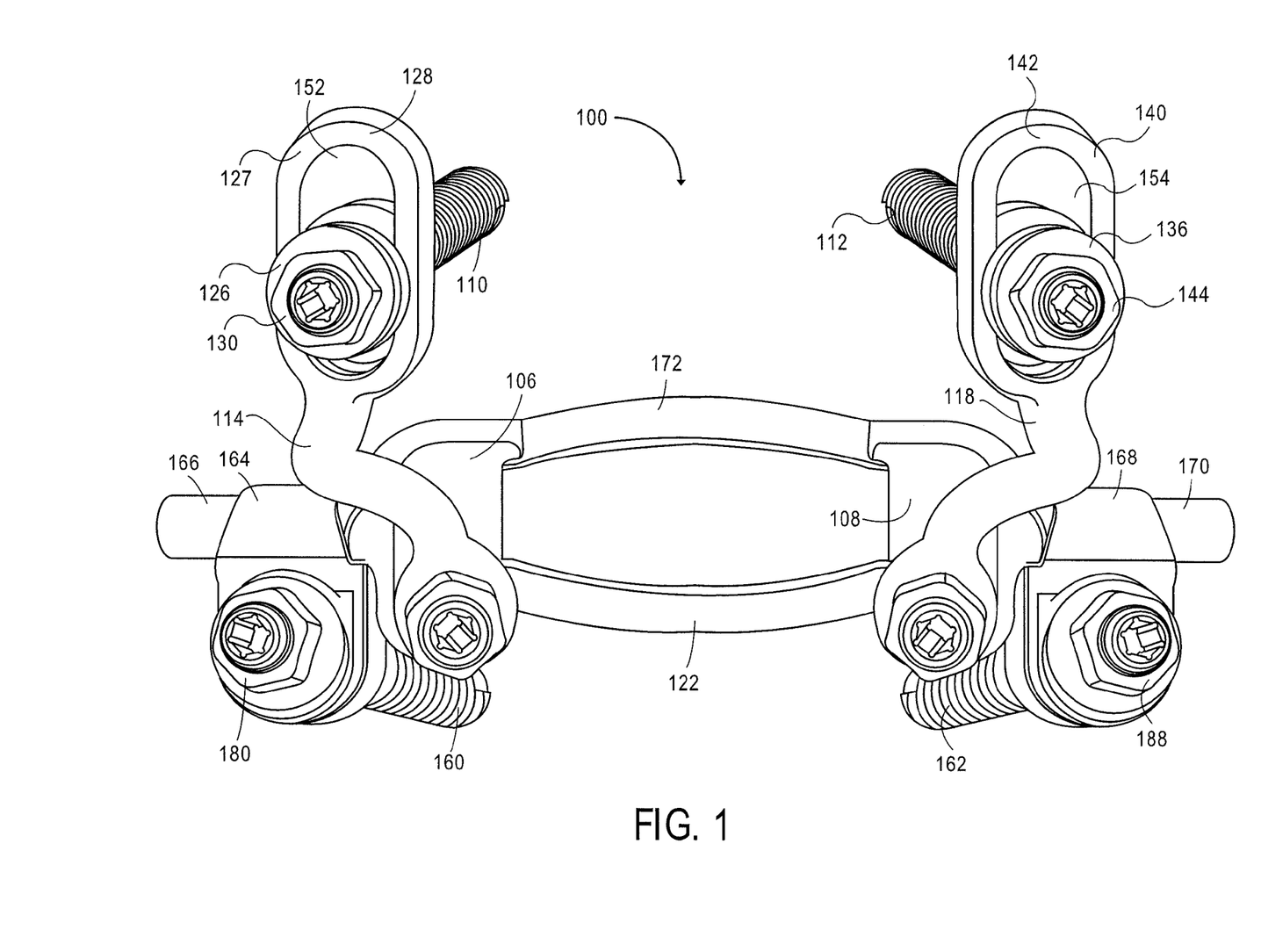
FIG. 1 is front elevational view of a dynamic spine prosthesis according to one embodiment of the invention.
Figure 2:
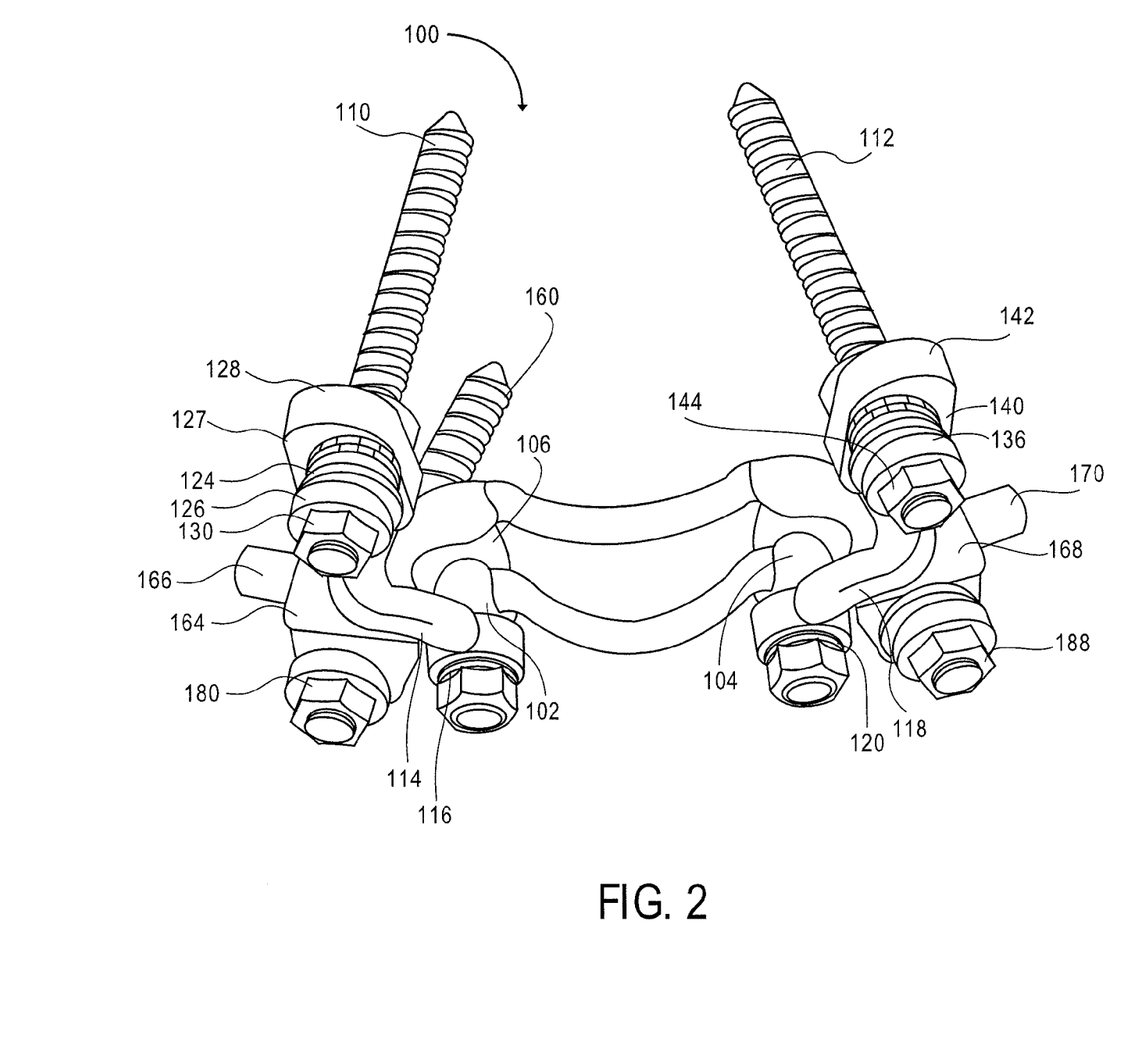
FIG. 2 is a perspective view of the dynamic spine prosthesis of FIG. 1.
Figure 3:
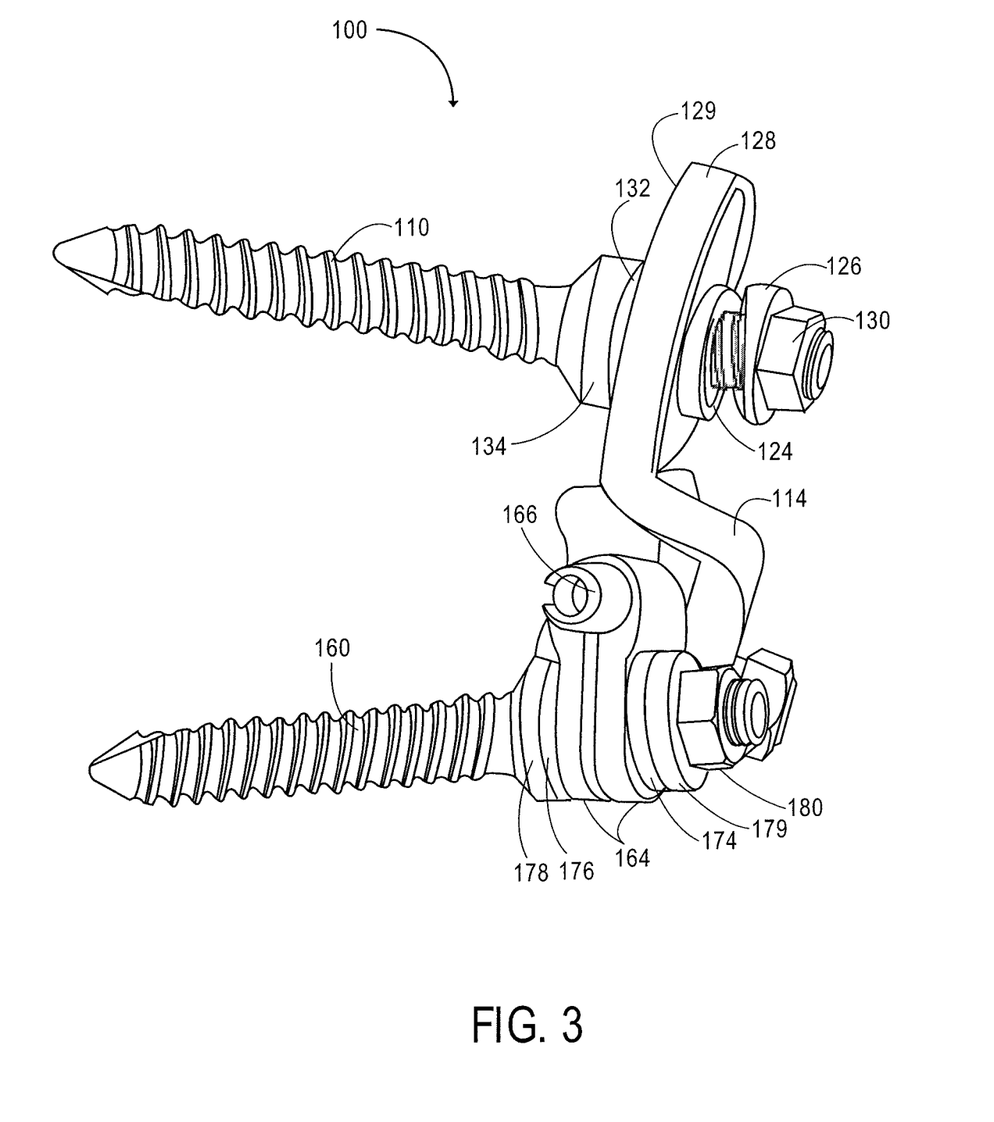
FIG. 3 is a right side elevational view of the dynamic spine prosthesis of FIG. 1.
Figure 4:
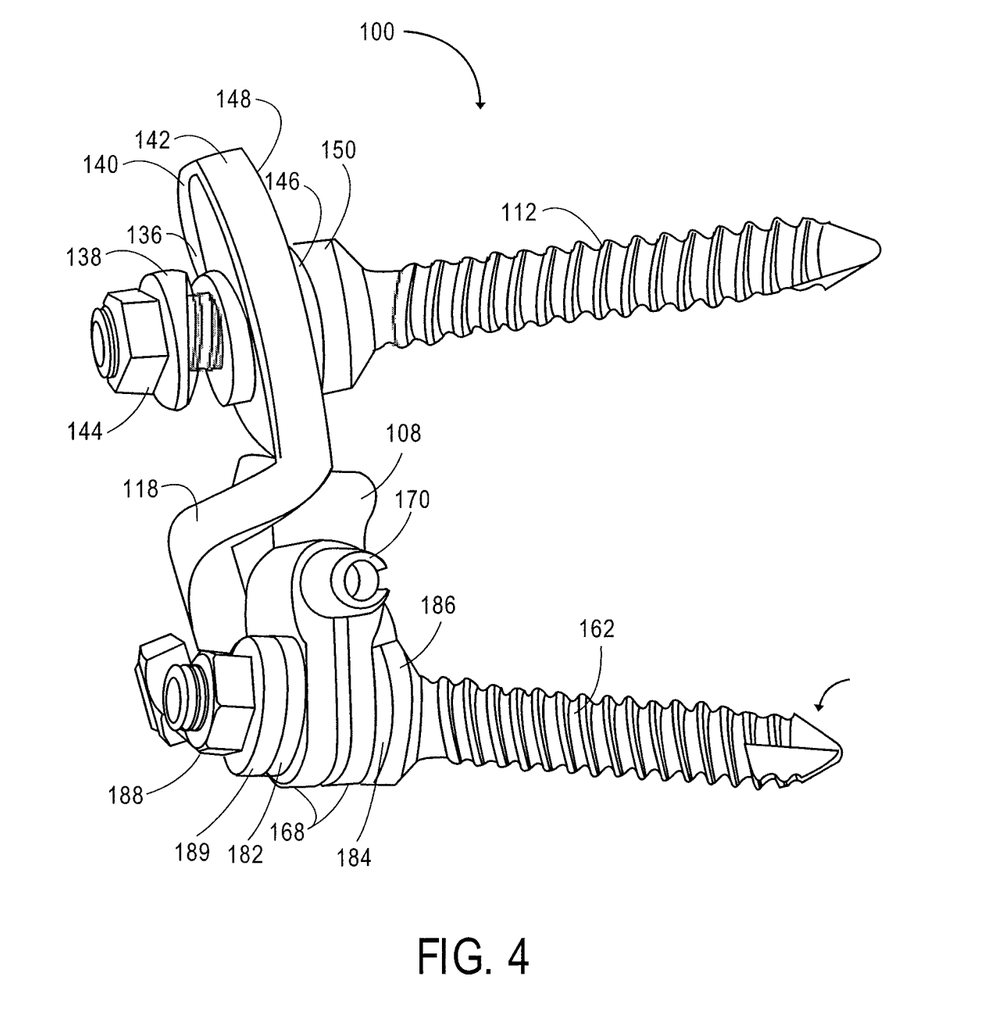
FIG. 4 is a left side elevational view of the dynamic spine prosthesis of FIG. 1.
Figure 5:
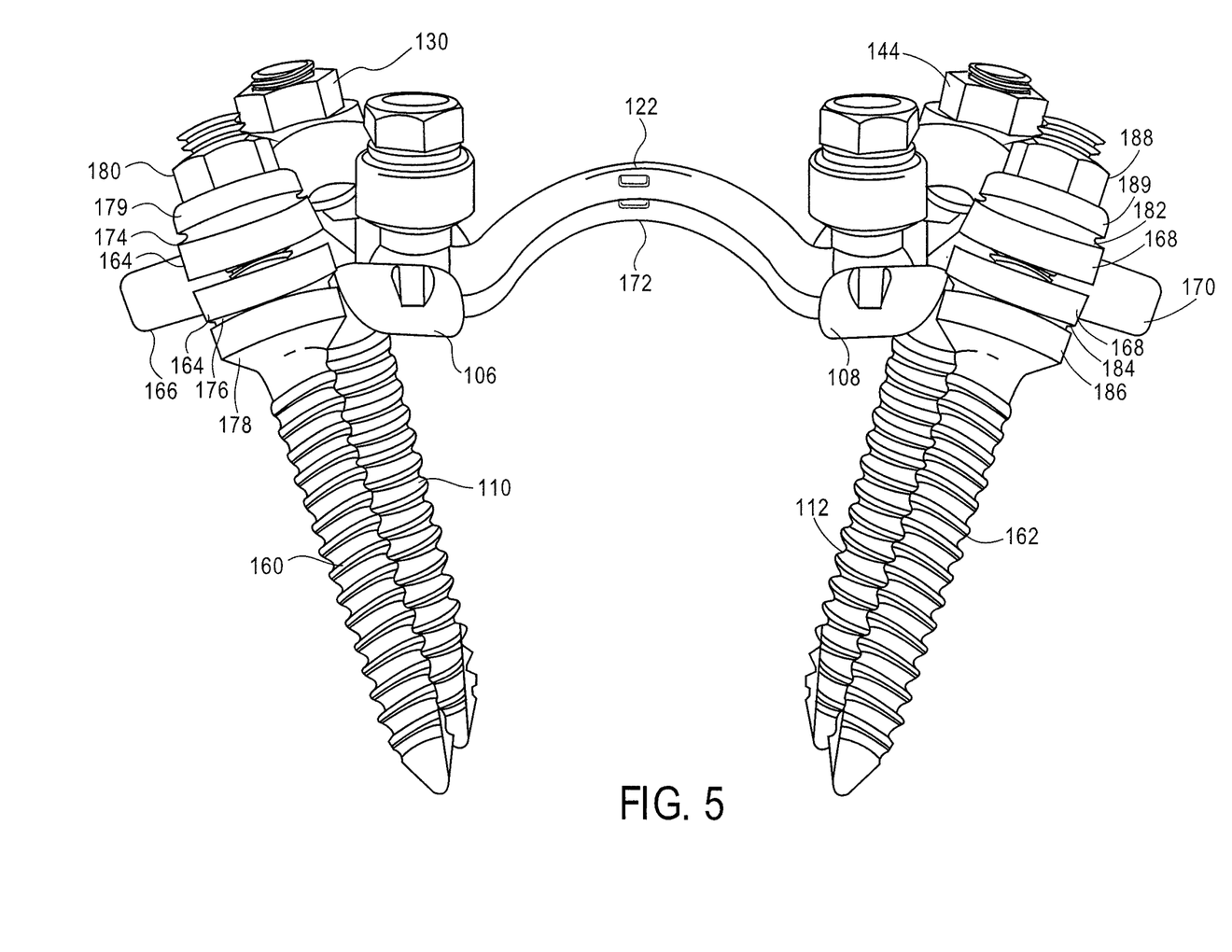
FIG. 5 is a bottom elevational view of the dynamic spine prosthesis of FIG. 1.

FIGS. 1-5 show one embodiment of a dynamic spine prosthesis according to this invention. In this embodiment, the dynamic spine prosthesis is an artificial facet joint prosthesis 100 providing left and right cephalad facet joint bearing elements 102 and 104 and left and right caudal facet joint bearing elements 106 and 108, respectively. When the cephalad facet joint bearing elements are attached to a superior vertebra and the caudal facet joint bearing elements are attached to an inferior vertebra, the corresponding left and right bearing elements move with respect to each other and bear against each other as the patient moves his or her back, which is often a combination of one of more of the following motions: flexion, extension, rotation and/or lateral bending.

The cephalad facet joint bearing elements attach to a superior vertebra via fixation elements, such as screws 110 and 112 having threaded bone entry portions. A left arm 114 extends generally downward from fixation element 110 to a support bar 116 to which left cephalad bearing element 102 is attached. Likewise, a right arm 118 extends generally downward from fixation element 112 to a support bar 120 to which right cephalad bearing element 104 is attached. A crossbar 122 extends between the right and left cephalad bearing elements.

Because of differences in patient anatomy, the cephalad portion of the dynamic spine prosthesis has adjustment mechanisms for adjusting the spatial relationship between the fixation elements and the other prosthesis components. First, the angle between the left cephalad fixation element 110 and the left support arm 114 may be adjusted and fixed in the adjusted position by rotating two angled washers 124 and 126 mounted on a proximal extension of fixation element 110 between the proximal face 127 of a fixation region 128 on the top end of arm 114 and a compression nut 130 or other tightening element. Because each washer 124 and 126 has a contact surface not perpendicular to the axis of fixation element 110, each washer 124 and 126 may be rotated about fixation element 110 to change the angle between arm 114 (and, therefore, cephalad bearing element 102) and fixation element 110. When the proper orientation has been set, tightening element 130 is tightened along a threaded proximal extension of fixation element 110 to keep the components in place.

In this embodiment, a partially spherical washer 132 is disposed between the distal face 129 of the left cephalad support arm's fixation region 128 rests in an annular channel 134 on fixation element 110 to provide firm contact between the distal face of the arm fixation region and the fixation element. Alternatively, a second pair of angled washers may be used in place of the partially spherical washer.

Similarly, the angle between the right cephalad fixation element 112 and the right support arm 118 may be adjusted and fixed in the adjusted position by rotating two angled washers 136 and 138 mounted on a proximal extension of fixation element 112 between the proximal face 140 of a fixation region 142 on the top end of arm 114 and a compression nut 144 or other tightening element. As on the left side, because each washer 136 and 138 has a contact surface not perpendicular to the axis of fixation element 112, each washer 136 and 138 may be rotated about fixation element 112 to change the angle between arm 118 (and, therefore, cephalad bearing element 104) and fixation element 112. When the proper orientation has been set, tightening element 144 is tightened along a threaded proximal extension of fixation element 112 to keep the components in place.

As on the left side, in this embodiment a partially spherical washer 146 disposed between the distal face 148 of the right cephalad support arm's fixation region 142 rests in an annular channel 150 on fixation element 112 to provide firm contact between the distal face of the arm fixation region and the fixation element. Once again, a second pair of angled washers may be used in place of the partially spherical washer.

An additional adjustment mechanism is provided by the oval shaped openings 152 and 154 of the fixation regions 128 and 142 of left and right cephalad support arms 114 and 118, respectively. The support arms 114 and 118 may be moved up or down with respect to fixation elements 110 and 112, respectively, before tightening compression screws 130 or 144 to further adjust the spatial relationships between cephalad facet bearing elements 102 and 104 and fixation elements 110 and 112. The cephalad support arms 114 and 118 may also be rotated about their respective fixation elements 110 and 112 before tightening.

The caudal facet joint prosthesis components may be adjusted with respect to their fixation elements as well. The caudal facet prosthesis bearing elements attach via screws or other fixation elements 160 and 162 to a vertebra inferior to the vertebra to which the cephalad components have been attached. Looking first on the left side, a clamp 164 mounted on fixation element 160 holds a left caudal support bar 166 extending from left caudal bearing surface 106. Likewise, a clamp 168 mounted on fixation element 162 holds a right caudal support bar 170 extending from right caudal bearing surface 108. A crossbar 172 extends between the left and right caudal bearing surfaces.

In this embodiment, the angle between the left caudal fixation element 160 and the left caudal clamp 164 may be adjusted by rotating a first partially spherical washer 174 (disposed proximal to clamp 464) with respect to a cap 179 beneath a compression screw 180 and/or by rotating a second partially spherical washer 176 (disposed distal to clamp 164) with respect to an annular channel 178 formed in fixation element 160. When the proper orientation has been achieved, compression screw 180 or other tightening element is tightened along a threaded proximal extension of fixation element 160 to fix these components in place. Alternatively, a pair of angled washers may be used in place of the partially spherical washers, as in the cephalad component. Likewise on the right side, the angle between the right caudal fixation element 162 and the right caudal clamp 168 may be adjusted by rotating a first partially spherical washer 182 (disposed proximal to clamp 168) with respect to a cap 189 beneath a compression screw 188 and/or by rotating a second partially spherical washer 184 (disposed distal to clamp 168) with respect to an annular channel 186 formed in fixation element 162. When the proper orientation has been achieved, compression screw 188 or other tightening element is tightened along a threaded proximal extension of fixation element 162 to fix these components in place. Alternatively, a pair of angled washers may be used in place of the partially spherical washers, as in the cephalad component, as before.

Because the various components of the present invention allows for significant adjustment and/or modular variability between the dynamic elements and the fixation elements, the device is particularly well suited for use in virtually all levels of the spine, and for virtually all anatomical variations, including adult males or females or even children. If desired, the fixation elements can incorporate bony in-growth and/or osteo-integration surfaces and/or materials, or the various fixation elements could be utilizes in conjunction with auxiliary fixation materials such as ceramic, crystalline, organic, polymeric or other types of bone cement or adhesives. Where the device fails for some reason, or revision is necessitated (such as, for example, where a young patient "grows out of" the device), a physician could access the device and disassemble those pieces necessary to be replaced, and then reassemble the same or a different size or configuration of the device, or assemble a fusion construct utilizing one or more of the original fixation elements already integrated within and/or attached to the patient's bones.

If desired, the devices of the present invention could be utilized with virtually any dynamic system, including those used in combination with an artificial spinal disc replacement device. Virtually all of the various embodiments disclosed here could be utilized, in various ways, in combination with artificial disc replacement devices, as well as nucleus repair systems and replacement devices, interbody spacers, dynamic stabilization devices, articulating rod and screw systems, posterior ligament or annular repair and/or augmentation devices, interspinous spacers, facet replacement and/or resurfacing devices, and the like. Use of the present devices in a dynamic system, in combination with an artificial disc replacement or repair, provides a solution for the total disc replacement contraindication of facet degeneration. Moreover, implantation of a total disc replacement device after removal of some or all of one or more of the facets and/or other intervening tissues (hard or soft), but prior to implantation of the dynamic device, provides a large, safe and repeatable access to the disc space, as well as aiding in any decompression of the joint that may be necessary. Such access facilitates passage of one or more components of the artificial disc replacement (or nucleus replacement, or annular repair material, and their respective tools) through the removed facet tissues via a lateral, posterior-lateral and/or posterior approach. The functions of the removed tissues can then be replaced by implanting the dynamic device as described herein. Of course, the dynamic devices disclosed herein (and the surgical removal of tissues to create one or more access paths) may be used unilaterally or bilaterally, depending on the nature of and stage of disease, and can be used at multiple levels of the spine of facet and/or other intervening tissues.

In various embodiments, a series of artificial dynamic components of differing shapes, sizes and/or orientations and/or lengths can be provided to accommodate different objectives, including alteration of dynamic element height/orientation relative to the fixation element, to accommodate different loading conditions due to other surgical treatments (i.e., artificial disc replacement of the same or other spinal level, annular repair, nucleus replacement, dynamic stabilization, interspinous spacer and/or adjacent level fusion and/or facet replacement devices). Moreover, to accommodate differing designs (i.e., constrained discs versus unconstrained discs) and/or arrangement/positioning of artificial disc replacement devices used on the same or different spinal levels, the dynamic elements could be of differing shapes, sizes, orientations and/or lengths to accommodate the different loading profiles induced or desired by the artificial disc replacement devices.

In one alternate embodiment, once the components of the device have been secured to the targeted vertebral bodies, one or more elastic compression devices or "bands" could be secured about the dynamic elements (or to the vertebral bodies themselves, or between other parts of the device, or any combination thereof). Properly positioned and/or tensioned, these "bands" would tend to keep the dynamic elements in contact and/or close proximity, even under extreme and/or unusual loading conditions, and thus reduce and/or eliminate the opportunity for the device to dislocate. Moreover, in the event that dislocation of the device did occur, the bands could prevent and/or limit motion of the dislocated joint (by holding the dynamic elements together), and thus reduce or eliminate damage to other tissues (such as the spinal cord, various other nerves and/or circulatory/connective tissues) resulting from the dislocation. In fact, the compression of the bands might make it possible to eventually "reduce" the dislocation and/or repair the dislocated device through external manipulation and/or minimally-invasive surgery. If desired, one or more "bands" could be secured between the dynamic elements of the device, or between the various surfaces, arms, cups, stems and/or cross-arms of the device components, with varying results.

In another alternative embodiment, the compression device could comprise an elastic or pliable material surrounded by a non-elastic housing, whereby the elastic material allows various movement of the dynamic elements (with resistance commensurate to the flexibility of the material), but the non-elastic housing acts as an ultimate "stop" to movement of the dynamic elements beyond a certain predetermined limit. Similarly, the "band" could comprise an elastic, non-elastic or rigid material, such as stainless steel cable, which desirably prevents relative motion of the elements of the device beyond a certain pre-defined maximum extension/flexion.

Advantageously and in contrast to conventional techniques where fusion and dynamic implants are implanted via an open procedure, a majority of the components of the present dynamic devices can be surgically implanted using minimally-invasive techniques alone or in combination with conventional open techniques. For example, all or most of the components of the device may be delivered through a cannula inserted through a small incision in the skin. To implant the device components, the physician can first create an access path through the skin and soft tissue (with a spinal needle and/or K-wire) to the targeted vertebral body. Desirably, non-invasive visualization, such as fluoroscopic or real-time MRI, is used to monitor the advancement of the needle and avoid damage to tissue structures such as muscles, tendons, ligaments, nerves, veins and/or the spinal cord itself. Once the access path has been created, a suitable cannula can be advanced through the tissues to the targeted bone. If necessary, progressively larger dilation catheters (such as the Access™ Dilation Port commercially available from Spinal Concepts of Austin, Tex.) can be used to introduce a cannula having a lumen large enough to accommodate passage of the components.

Depending upon the patient's condition and the desired surgical outcome, as well as the surgeon's preference, the present embodiment can facilitate the repair and replacement/augmentation of the facet joints in a minimally-invasive, limited-open (or modified-open) and/or fully-open surgical procedure. For example, where facet joint replacement is deemed necessary, but removal of soft and/or hard tissues in and/or adjacent the spinal canal is not warranted or desired (such as where spinal stenosis and nerve impingement is not a significant concern), the repair and/or replacement of one or more facet joints can be accomplished in a least-invasive fashion, using one or more cannulae to implant the prosthesis and associated distal hardware. Alternatively, where removal of the facet joints and/or lamina is necessitated, such a procedure can be accomplished through a combination of open, semi-open and/or minimally invasive procedures (which will be referred to herein as a modified-open or mini-open procedure) to minimize damage and/or disruption to surrounding soft-tissue structures. In such a procedure, one or more of the facet joint capsules can be exposed through an open incision (to allow easy resection and removal of the facet joint and/or surrounding anatomical structures), and the components of the dynamic device can be delivered through a cannula or other minimally-invasive delivery method.

Various alternative embodiments of the present invention could incorporate laminar, spinous process, pedicle-based and/or vertebral body fixation elements, or any combinations thereof, ultimately desirous for replacing and/or augmenting the natural facets and other intervertebral tissues. Of course, the systems disclosed herein may be anchored to the vertebral bodies in various ways, including the use of screw threads or stems, with or without using cement and/or bony ingrowth surfaces to augment fixation.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A dynamic spine prosthesis comprising:
   a fixation element having an elongated bone entry portion defining a longitudinal axis;
   a dynamic spine prosthesis component connected to the fixation element at a connection location by an adjustable connection, the adjustable connection comprising first and second washers each rotatably supported by the fixation element and each having an angled contact surface in a plane not perpendicular to the longitudinal axis of the fixation element, the connection location being between the bone entry portion and the first and second washers, wherein the angled contact surfaces of the first and second washers are in contact with each other, wherein each of the first and second washers can be rotated about the fixation element to change the angle between a portion of the dynamic spine prosthesis component and the fixation element, and wherein the first washer includes an angled surface on a bottom most surface and the second washer includes an angled surface on a top most surface; and
   a third washer between the dynamic spine prosthesis and the bone entry portion of the fixation element.

2. The dynamic spine prosthesis of claim 1 further comprising a tightening element having a first position enabling movement between the first and second washers and the fixation element and a second position preventing movement between the washers and the fixation element.

3. The dynamic spine prosthesis of claim 2 wherein the tightening element is a compression nut mounted on a threaded extension of the fixation element.

4. The dynamic spine prosthesis of claim 1 wherein the adjustable connection further comprises a structural attachment element supporting the dynamic spine prosthesis component, the structural attachment element having a first position in which the dynamic spine prosthesis component is movable with respect to the structural element and a second position in which the dynamic spine prosthesis component is fixed with respect to the structural element.

5. The dynamic spine prosthesis of claim 1 wherein the dynamic spine prosthesis component is a facet joint prosthesis comprising an articulation surface configured to articulate with a corresponding facet joint element.

6. The dynamic spine prosthesis of claim 1, wherein the third washer comprises a partial spherical surface.

7. The dynamic spine prosthesis of claim 1 wherein each of the contact surfaces of the first and second washers is not perpendicular to the axis of the fixation element.

8. A dynamic spine prosthesis comprising:
a first cephalad facet joint bearing element and a second cephalad facet joint bearing element;
a first crossbar extending from the first cephalad facet joint bearing element to the second cephalad facet joint bearing element;
a first caudal facet joint bearing element and a second caudal facet joint bearing element;
a second crossbar extending from the first caudal facet joint bearing element to the second caudal facet joint bearing element;
a cephalad fixation element having an elongated bone entry portion defining a longitudinal axis for attaching the first cephalad joint bearing element to a first vertebra;
a caudal fixation element having an elongated bone entry portion defining a longitudinal axis for attaching the first caudal joint bearing element to a second vertebra; and
a dynamic spine prosthesis component connected to the cephalad fixation element at a connection location by an adjustable connection,
the adjustable connection comprising first and second washers each rotatably supported by the fixation element and each having an angled contact surface in a plane not perpendicular to the longitudinal axis of the fixation element, wherein the angled contact surfaces of the first and second washers are in contact with each other, and wherein each of the first and second washers can be rotated about the fixation element to change the angle between a portion of the dynamic spine prosthesis component and the fixation element.

9. A dynamic spine prosthesis comprising:

a fixation element having an elongated bone entry portion defining a longitudinal axis;

a dynamic spine prosthesis component connected to the fixation element at a connection location by an adjustable connection, the adjustable connection comprising first and second washers each rotatably supported by the fixation element and each having an angled contact surface in a plane not perpendicular to the longitudinal axis of the fixation element, the connection location being between the bone entry portion and the first and second washers, wherein the angled contact surfaces of the first and second washers are in contact with each other; and a third washer between the dynamic spine prosthesis and the bone entry portion of the fixation element.

* * * * *